United States Patent [19]

Mathre et al.

[11] Patent Number: 5,574,176
[45] Date of Patent: Nov. 12, 1996

[54] SYNTHESIS OF AN INTERMEDIATE FOR THE PREPARATION OF 5,6-DIHYDRO-(S)-4-(ETHYLAMINO)-(S)-6-METHYL-4H-THIENO [2,3-B]THIOPYRAN-2-SULFONAMIDE 7,7-DIOXIDE INTERMEDIATES AND RELATED COMPOUNDS

[75] Inventors: David J. Mathre, Skillman; Paul Sohar, Warren; Lynn M. Brown, Clark, all of N.J.

[73] Assignee: Merck & Co., Inc., Rahway, N.J.

[21] Appl. No.: 430,214

[22] Filed: Apr. 26, 1995

[51] Int. Cl.⁶ ...................... C07D 333/18; C07D 495/04
[52] U.S. Cl. .................................................. 549/66; 549/23
[58] Field of Search ................................... 549/66, 62, 23

[56] References Cited

U.S. PATENT DOCUMENTS

| 4,113,968 | 9/1978 | Mori et al. | 560/124 |
| 4,797,413 | 1/1989 | Baldwin et al. | 514/432 |
| 4,968,814 | 11/1990 | Blacklock et al. | 549/66 |
| 4,968,815 | 11/1990 | Blacklock et al. | 549/66 |

OTHER PUBLICATIONS

Blacklock, T. J. et al., *J.Org. Chem.*, 58, pp. 1672–1679 (1993). III.

*Primary Examiner*—Joseé G. Dees
*Assistant Examiner*—Deborah Lambkin
*Attorney, Agent, or Firm*—Sylvia A. Ayler; Mark R. Daniel

[57] ABSTRACT

This invention is concerned with an improved process for the synthesis of and intermediate en route to 5,6-dihydro-(s)-4-(ethylamino)-(s)-6-methyl-4h-thieno[2,3-b]thiopyran-2-sulfonamide 7,7-dioxide and related compounds. The instant process reduces the reaction time for the synthesis of the key intermediate from 3 to 4 days to from about 2 to about 4 hours while retaining the high enantiomeric purity of the product.

5 Claims, No Drawings

SYNTHESIS OF AN INTERMEDIATE FOR THE PREPARATION OF 5,6-DIHYDRO-(S)-4-(ETHYLAMINO)-(S)-6-METHYL-4H-THIENO[2,3-B]THIOPYRAN-2-SULFONAMIDE 7,7-DIOXIDE INTERMEDIATES AND RELATED COMPOUNDS

BACKGROUND OF THE INVENTION

The current therapy for control of elevated intraocular pressure (IOP) or ocular hypertension which is believed to be a factor in the onset and progress of glaucoma is typically effected with a variety of topically applied agents which fall within four categories: β-blockers, sympathomimetic agents, parasympatho-mimetic agents and cholinesterase inhibitors. The adjuvant oral administration of a carbonic anhydrase inhibitor (CAI) is practised when the above-described topical agent's side effects limits its use and/or it fails to achieve adequate IOP control. The orally active CAI's can exhibit serious side-effects such as anorexia, gastrointestinal upset and parasthesias. Therefore an intense and ongoing search has been mounted for a topically active CAI that would not exhibit such side effects due to the route of administration and inherent target organ specificity. This search has resulted in the discovery of a class of compounds by Baldwin et al (U.S. Pat. No. 4,797,413) of general formula:

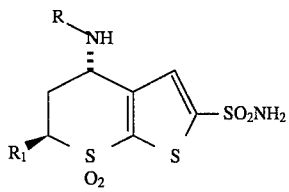

wherein R and $R_1$ are lower alkyl, especially dorzolamide, wherein R is ethyl and $R_1$ is methyl.

U.S. Pat. No. 4,797,413 discloses a process for preparing the racemic modification of the alkyl 3-(thien-2-ylthio)butyrate and its homologs. The prior art process comprises addition of the 2-thienyl-thiol (II) across the double bond of a substituted acrylic acid (IV) to yield the acid I:

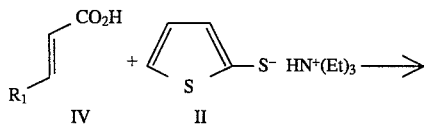

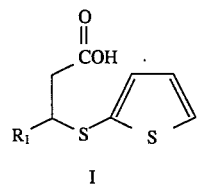

followed by synthesis of the final diastereomeric product, the isomers of which must be separated and each resolved to obtain the most active (S,S)-enantiomer. The isomer separations result in an automatic loss of the bulk of the chemical product.

U.S. Pat. No. 4,968,815 discloses a process for preparing the acid of structural formula I:

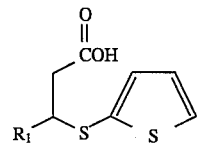

which comprises treating a nucleophile of structure II with a compound of structure III as shown:

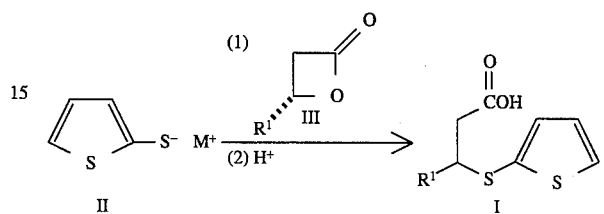

wherein the R groups are as hereinafter defined. U.S. Pat. No. 4,968,814 and Blacklock et al., J. Org. Chem., 1993, 58, 1672–1679 also teaches a process for preparing the chiral intermediate formula I. However, these prior an processes involve many steps, are expensive and very time consuming.

It is therefore an object of this invention to provide a process for the synthesis of acid (I) for the synthesis of a chiral final product (V), dorzolamide, more economically than previously possible.

SUMMARY OF THE INVENTION

This invention is concerned with an improved process for the synthesis of the acid of structural formula I

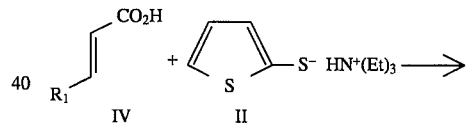

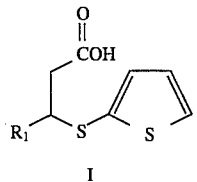

wherein $R_1$ is described below. The acid is a key intermediate in the synthesis of the compound of formula V:

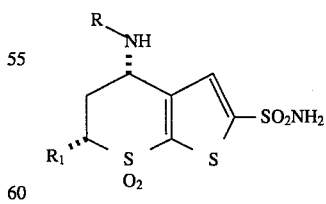

wherein R and $R_1$ are lower alkyl, especially dorzolamide, wherein R is ethyl and $R_1$ is methyl, a carbonic anhydrase inhibitor topically effective in the treatment of ocular hypertension and glaucoma.

The instant process reduces the reaction time from 3 to 4 days to from about 2 to about 4 hours while retaining the high enantiomeric purity of the product.

DETAILED DESCRIPTION OF THE INVENTION

The novel process of the present invention can be depicted as shown in Scheme I:

SCHEME 1

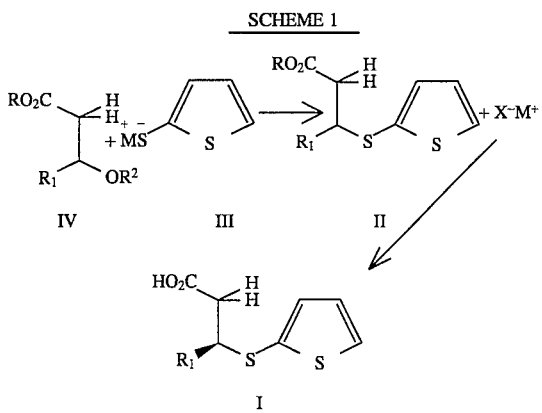

Preparation of a Compound of structural formula I:

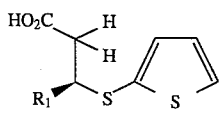

wherein $R_1$ is hydrogen, $C_{1-4}$ alkyl, or $C_{1-4}$ alkoxy-$C_{1-4}$alkyl, comprises treating a compound of formula III:

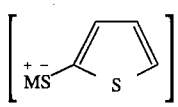

wherein $M^+$ is $(C_2H_5)_3 NH^+$, $Na^+$, $K^+$, or $Li^+$ with a compound of structural formula IV:

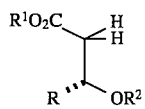

wherein R and $R^1$ independently are hydrogen, or $C_{1-4}$ alkyl, and $R^2$ is tosyl, mesyl, p-methoxy benzenesulfonyl, p- or m-chloro-, or bromo-, benzenesulfonyl or p-nitrobenzenesulfonyl in formamide or a mixture of an ethereal solvent and formamide at a temperature of about 41° C. to 60° C. for about 2 to about 4 hours to produce Compound II, treating Compound II

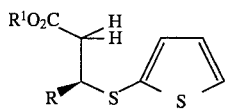

with 8:1 acetic acid/strong mineral acid solution at a temperature of about 50° to 118° C. for about 5 to about 10 hours to produce Compound I, wherein $R^1$=H and isolating Compound I. The mineral acid can be hydrochloric acid, sulfuric acid, phosphoric acid, hydrobromic acid, and the like.

The alkylation can be conducted preferrably at about 41°–45° C., until the reaction is substantially complete in about 2 to about 4 hours. The reaction time is shortened from 3 to 4 days to 2 to about 4 hours as a result of the heating, which is done without loss of chirality at the chiral carbon. This improvement was unexpected and significant because generally at temperatures above 40° C. a competing elimination of tosic acid reaction would be expected. Under certain reaction conditions elimination of a proton adjacent to the ester, as well as the tosylate, produces the α,β-unsaturated ester. This can undergo a 1,4-addition with 2-(lithiomercapto)thiophene to produce a racemic mixture of the undesired (R)-enantiomer, in addition to the desired (S)-enantiomer. With the instant invention, the temperature range is high enough to allow for an increase in reaction rate, but low enough to prevent the undesired elimination reaction.

The reaction can be quenched by addition of the reaction mixture to aqueous ethyl acetate, or addition of aqueous ethyl acetate to the reaction mixture. Ethyl acetate can be replaced by n-butyl acetate, methyl t-butyl ether, methyl ethyl ketone, methyl isobutyl ketone, and the like. Hexane can be replaced by pentane, cyclohexane, cyclopentane, heptane, petroleum ether, and the like. Brine can be composed of aqueous solutions of sodium chloride, calcium chloride, sodium sulfate, calcium sulfate, magnesium sulfate, potassium carbonate, and the like.

The hydrolysis reaction of the ester to the acid can be conducted preferrably at about 50° to 80° C. The instant acid hydrolysis of the ester is significant in that hydrolysis in the heterogeneous reaction medium of HCl and $H_2O$ produces, in addition to the desired (S)-3-(2-thienylthio)butyric acid, the regioisomeric (S)-3-(3-thienylthio)butyric acid and the corresponding ring closed product. Formation of these undesired regioisomers is reduced or eliminated through use of the instant homogeneous acetic acid and strong mineral acid hydrolysis conditions.

The hydrolysis reaction can be worked up through distillation and extraction, as outlined in the experimental section. Alternatively, the distillation can be performed, and the crude reaction mixture carried on as a through-process in the subsequent ring closure step.

Acid I is then converted, through a series of steps, to dorzolamide V. The sequence is shown in Scheme 2.

Scheme 2

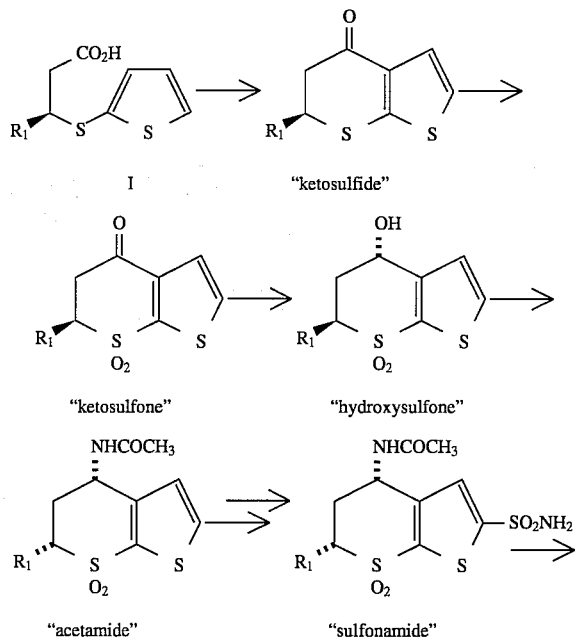

-continued
Scheme 2

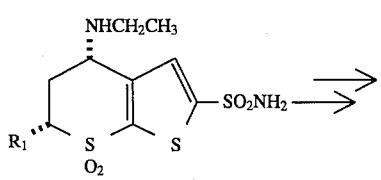

"dorzolamide free base"

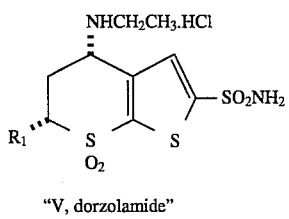

"V, dorzolamide"

The reaction steps are exemplified by the Examples that follows. The product of the novel process of this invention is a topically effective carbonic anhydrase inhibitor useful in the treatment of ocular hypertension. It is administered topically to the eye usually as a solution, comprising about 0.1% to .15% by weight of compound, one or two drops at a time, one to four times a day.

EXAMPLE 1

Thiophene (65.3 mL, 815.3 mmol) and anhydrous THF were added to a 5 L 3-neck round bottomed flask equipped with a reflux condenser, nitrogen inlet robe, mechanical stirrer, and thermocouple. The solution was cooled to $-5°$ to $-10°$ C., and n-butyl lithium (395 mL, 2.0M in hexanes) was added at a rate that allowed the temperature to remain below $5°$ C. The solution was allowed to age at $0°$ to $-5°$ C. for 1 hour. Powdered sulfur (25.3 g, 791 mmol) was added to this solution in portions, so that the temperature of the reaction mixture remained below $5°$ C. The sulfur dissolved in this rapidly stirring solution within 5 minutes, and an assay indicated that formation of 2-(lithiomercapto)thiophene was complete after the sulfur dissolved. The temperature was maintained at $0°$ to $5°$ C., and formamide (722 mL), which had been degassed with nitrogen, was added. The temperature increased to $14°$ C. upon addition of formamide, and the solution became biphasic. Solid methyl (R)-3-(p-toluenesulfonyloxy)butyrate was then added, and the reaction mixture heated to $41°–45°$ C.

The reaction course was monitored by HPLC, and the reaction was found to be complete within 2 to 4 hours. It was necessary to sample from both layers during monitoring due to the differential solubilities of reactants and products in the two layers. To the reaction mixture was added $H_2O$/ethyl acetate (2:1, 2162 mL). The mixture was allowed to stir for 30 minutes at $25°$ C., and the aqueous layer was then separated. The aqueous layer was washed with ethyl acetate/hexane (1:1, 370 mL). The organic layers were combined, and washed with brine (420 mL).

The product was concentrated to an oil and isolated chromatographically. The conditions for chromatography are a silica gel support with 10% ethyl acetate in hexanes as the eluting solvent. The second major fraction ($R_f$=0.52) represented the desired product. The product was converted to the acid by removing the ethyl acetate in vacuo, and adding water (350 mL). Distillation continued until the final volume was 260 mL. The product was then subjected to hydrolysis conditions to form the carboxylic acid.

Analysis: $^1$H NMR (CDCl$_3$) δ 7.41 (m, 1H), 7.17 (m, 1H), 7.02 (m, 1H), 3.69 (s, 3H), 3.39 (m 1H), 2.67 (dd, 1H, J=15.7, J=6.4 Hz), 2.42 (dd, 1H, J=15.7, 8.2 Hz); $^{13}$C NMR (CDCl$_3$) δ 171.6, 136.2, 130.9, 130.7, 127.7, 51.7, 41.8, 41.4, 20.7:

Chirality was determined on the corresponding acid after hydrolysis. Chirality >97.7:2.3. The acid was converted to the 3,5-dimethylanilide derivative, and analyzed on a column containing the (R,R) GEM CSP (Regis Technologies) with a mobile phase of 90:10 hexane/THF. Derivatization procedure: The acid (1 eq.) in $CH_2Cl_2$ was treated with (2-ethoxy-1-ethoxycarbonyl-1,2-dihydroquinoline (EEDQ, 111 eq.)). This was allowed to stir for 30 minutes. 3,5-Dimethylaniline was added, and the reaction allowed to proceed for 15 minutes. The organic layer was then washed with 1N HCl (2×10 mL), $H_2O$ (2×10 mL), and saturated NaHCO$_3$ (10 mL).

Enantiomeric purity of the chiral ester can be determined directly by supercritical fluid chromatography using a Chiralpak AD column (Chiral Technologies, Inc.) Conditions: 300 bar $CO_2$ containing 2 vol. % methanol, 1 mL/min, $35°$ C., detection with UV, 235 nm. The "S"-enantiomer elutes at 7.3 min and the "R"-enantiomer elutes at 8.1 min.

EXAMPLE 2

A solution of the reaction mixture from the alkylation reaction in ethyl acetate (137 mL, ca. 30 g, 0.11 mole) was concentrated to a volume of 96 mL. Water was added (2×25 mL), and the volume reduced to 25 mL. Glacial acetic acid (96 mL) and concentrated HCl (12 mL) were added. The reaction mixture was heated to $80°–85°$ C. for 8 hours. A vacuum distillation was then performed to remove acetic acid. Water (2×25 mL) was added, and the distillation continued. To the oil was added ethyl acetate (60 mL) and water (60 mL), and the layers separated. The aqueous layer was washed with ethyl acetate (30 mL). The organic layers were combined and water (60 mL) was added. The pH of the aqueous system was adjusted to 8.5 by slow addition of 50% NaOH, and the layers separated. Water (30 mL) was again added to the organic layer, and the pH again adjusted to 8.5. To the combined aqueous layers was added toluene (90 mL) and concentrated HCl (6.8 mL). The mixture was stirred so that the white precipitate, which formed upon acidification, dissolved. The layers were separated, and the aqueous layer again washed with toluene (45 mL). The organic layers were combined and washed with brine (50 mL). This reaction mixture was then treated with trifluoracetic anhydride, to produce the next product in the reaction sequence. However the yield ranges from 84–87%.

Analysis: $^1$H NMR (CDCl$_3$) δ 7.45 (d, 1 H, J=5.5), 7.02 (d, 1 H, J=5.5), 3.80 (ddq, 1 H, J=11.4, J=3.2, J=6.9), 2.89 (dd, 1 H, J=3.2, J=16.8), 2.69 (dd, 1 H, J=11.4, J=16.8), 1.49 (d, 3 H, J=6.9).

Employing the procedures substantially as described in the foregoing experimental but substituting for the (R)-3-(p-toluenesulfonyloxy)butyrate used therein comparable amounts of the 3-hydroxy esters shown in the following table, there are produced the (S)-3-(2-thienylthio)alkanoic acids also described in the following table:

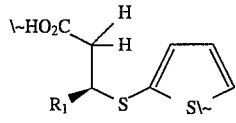

| $R_1$ |
|---|
| $CH_3O(CH_2)_2-$ |
| $C_2H_5O(CH_2)_2-$ |
| $CH_3O(CH_2)_2-$ |
| $C_2H_7O(CH_2)_3-$ |
| $C_2H_5O(CH_2)_2-$ |
| $C_2H_5O(CH_2)_3-$ |
| $C_4H_9O(CH_2)_2-$ |
| $CH_3O(CH_2)_4-$ |
| $C_2H_5-$ |
| $C_3H_7-$ |

What is claimed is:

1. Preparation of a Compound I of structural formula:

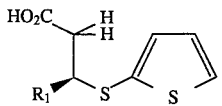

wherein $R_1$ is hydrogen, $C_{1-4}$ alkyl, or $C_{1-4}$ alkoxy-$C_{1-4}$alkyl, comprising treating a compound III of structural formula:

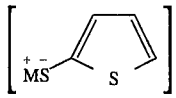

wherein $M^+$ is $(C_2H_5)_3NH^+$, $Na^+$, $K^+$, or $Li^+$ with a compound IV of structural formula:

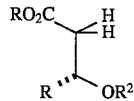

wherein R and $R_1$ independently are hydrogen, or $C_{1-4}$ alkyl, and $R_2$ is tosyl, mesyl, p-methoxy benzenesulfonyl, p- or m-chloro-, or bromo-, benzenesulfonyl or p-nitrobenzenesulfonyl in formamide or a mixture of an ethereal solvent and formamide at a temperature of about 41° C. to 60° C. for about 2 to about 4 hours to produce Compound II, treating Compound II

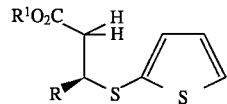

with about 8:1 acetic acid/strong mineral acid solution at a temperature of about 50° to 118° C. for about 5 to about 10 hours to produce Compound I and isolating Compound I.

2. The process of claim 1 wherein R and $R_1$ are methyl, $R_2$ is tosyl and $M^+$ is $(C_2H_5)_3NH^+$ or $Li^+$.

3. The process of claim 1 wherein the ethereal solvent is formamide, the strong mineral acid is hydrochloric acid, sulfuric acid, phosphoric acid, or hydrobromic acid and the temperature is 41° C. to 45° C.

4. The process of claim 3 wherein R and $R_1$ are methyl, $R_2$ is tosyl and $M^+$ is $(C_2H_5)_3NH^+$ or $Li^+$.

5. The process of claim 3 wherein the strong mineral acid is hydrochloric acid.

* * * * *